(12) United States Patent
Kumar et al.

(10) Patent No.: US 6,986,660 B2
(45) Date of Patent: Jan. 17, 2006

(54) RETAINING SCREW WITH RENTENTIVE FEATURE

(75) Inventors: Ajay Kumar, Palmdale, CA (US); Ines Aravena, Camarillo, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 175 days.

(21) Appl. No.: 10/302,253

(22) Filed: Nov. 22, 2002

(65) Prior Publication Data

US 2003/0224331 A1 Dec. 4, 2003

Related U.S. Application Data

(60) Provisional application No. 60/385,814, filed on Jun. 4, 2002.

(51) Int. Cl.
*A61C 13/277* (2006.01)
(52) U.S. Cl. ...................................... 433/173; 433/174
(58) Field of Classification Search ................ 433/172, 433/173, 174
See application file for complete search history.

(56) References Cited

U.S. PATENT DOCUMENTS

| | | | | |
|---|---|---|---|---|
| 4,927,363 | A | * | 5/1990 | Schneider .................... 433/173 |
| 5,269,686 | A | * | 12/1993 | James ......................... 433/174 |
| 5,711,669 | A | | 1/1998 | Hurson ........................ 433/174 |
| 5,733,122 | A | * | 3/1998 | Gordon ........................ 433/172 |
| 5,890,897 | A | * | 4/1999 | Kruger et al. ................. 433/75 |
| 6,168,436 | B1 | * | 1/2001 | O'Brien ....................... 433/173 |
| 6,280,193 | B1 | * | 8/2001 | Peltier ........................ 433/174 |
| 6,283,753 | B1 | * | 9/2001 | Willoughby ................. 433/172 |
| 6,447,295 | B1 | | 9/2002 | Kumar et al. ................ 433/172 |

FOREIGN PATENT DOCUMENTS

DE 297 10 520 U1 * 10/1997
WO WO 02/24 104 * 3/2002

* cited by examiner

*Primary Examiner*—Ralph A. Lewis
(74) *Attorney, Agent, or Firm*—Conley Rose, P.C.

(57) ABSTRACT

A dental retaining screw used to secure dental components, such as abutments, copings, and prosthesis to dental implants. The screw having a locking mechanism adapted to prevent the screw from loosening during shipping or while experiencing vibrations. The locking mechanism includes a locking component and biasing members located in the head portion of the retaining screw.

8 Claims, 2 Drawing Sheets

RETAINING SCREW WITH RENTENTIVE FEATURE

CROSS-REFERENCE TO RELATED APPLICATIONS

This application claims benefit of priority of U.S. Provisional Application Ser. No. 60/385,814 filed Jun. 4, 2002.

FIELD OF THE INVENTION

The present invention relates generally to the field of dental implantology and, more specifically, to retaining screws used to secure dental components, such as abutments, copings, and prosthesis to dental implants.

BACKGROUND OF THE INVENTION

Retaining screws in the field of dental implantology or dental prosthetics are very important since they are used to fasten and hold together various dental components. These retaining screws, for example, fasten the dental abutment to the dental implant. Unfortunately, prior dental retaining screws tend to loosen over time and also need internal threads inside the abutment to prevent the screw from falling out. The loosening of these screws has caused many problems, and much effort has been devoted to solving these problems.

Dental retaining screws are typically fabricated from titanium. On one hand, titanium is ideal for this indication since it is strong, light-weight, and biocompatible. On the other hand though, titanium has a high coefficient of friction that makes it very susceptible to loosening over time. Specifically, a large percentage of the torque applied to a dental retaining screw is lost to overcoming the high frictional contact between the screw threads and threaded bore of the implant and between the screw head and seating surface of the abutment. According to some estimates, approximately 50% of the applied torque is lost in overcoming the mating friction under the screw head; and 40% of the applied torque is lost in the threads. As such, only about 10% of the applied torque exerted on the screw head is actually exerted as preload or-tensile force stretching and tightening the screw.

Retaining screws tend to loosen in dental applications also because these screws are exposed to large loads and extended vibrations. Occlusal forces from chewing, talking, grinding, brushing, etc. continuously load the prosthetic tooth and accompanying retaining screw. These forces, over time, can decrease the preload and loosen the screw. Once the screw loosens, the joint between the prosthetic components can open or form gaps. The dental components, such as the prosthesis, the abutment, and the screw, can then bend or even break.

Over the years, many solutions have been proposed to reduce the occurrence of titanium screws loosening in dental applications. One solution is to increase the applied torque to the screw. This solution has limitations since the retaining screws can be tighten or loaded above the yield point of the material. In this instance, the screw can be permanently damaged and elastically unable to return to its original shape and position. Further yet, the maximum, attainable preload can be lessened if the screw is permanently damaged and deformed.

Many other solutions have been devoted to reducing the coefficient of friction either between the screw head and the mating surface of the dental component or between the screw threads and threaded bore of the implant. In some instances, screws have been made of gold-alloy material to reduce the co-efficient of friction, but their soft material causes deformation of their threads upon tightening.

In other instances, surface coatings have been placed on the retaining screw to reduce the coefficient of friction. U.S. Pat. No. 6,447,295, entitled "Diamond-Like Carbon Coated Dental Retaining Screws" and incorporated by reference herein, teaches a retaining screw coated with diamond-like carbon. Further, U.S. Pat. No. 5,711,669, entitled "High Load Factor Titanium Dental Implant Screw" teaches a retaining screw coated with a soft, deformable, biocompatible material that is malleable and subject to cold flow.

These coatings can reduce the coefficient of friction of the retaining screw, but the coatings have disadvantages. First, the coatings can be expensive. Additionally, they can wear over time or become removed or scraped during tightening. Further, although they can reduce the coefficient of friction, they do not prevent or inhibit the retaining screw from loosening or losing preload due to occlusal forces, vibrations during masticulation, and the like.

It would be advantageous to have a dental retaining screw that could be used to secure prosthetic components to a dental implant yet not be prone to loosen or fall out from the abutment.

BRIEF SUMMARY OF PREFERRED EMBODIMENTS OF THE INVENTION

The present invention is directed toward dental retaining screws used to secure dental components, such as abutments, copings, analogs, cuffs, healing members, and prosthesis to dental implants. The retaining screw has a proximal end with a locking mechanism. This mechanism includes a moveable locking component and a biasing member that are disposed in a housing formed as a bore.

The dental component includes an internal cavity with a locking mechanism along the interior surface of the cavity. The retaining screw fits inside this cavity and seats on a ledge to connect the dental component and implant. When the retaining screw is placed inside the abutment, the screw will not loosen and fall out. Specifically, the biasing member biases the locking component partially out of the housing to engage and lock with the locking mechanism of the dental component. The locking mechanisms of the retaining screw and dental component, thus, engage to prevent the screw from rotating or losing preload while tightened and connected to the implant.

One important advantage of the present invention is that once the retaining screw is tightened to a selected torque level, the locking mechanisms prevent or reduce the possibility that the retaining screw will loosen. The retaining screw will not tend to loosen even when exposed to large loads and extended vibrations, such as occlusal forces from chewing, clinching, grinding, talking, brushing, etc. Hence the stability of the dental implant system is improved and a secure and reliable fastening mechanism or coupling is provided between the dental component and the dental implant.

As a further advantage, the locking mechanisms of both the dental component and retaining screw are biocompatible and resistive to corrosion. The retaining screw is also relatively inexpensive to manufacture.

Accordingly, the present invention comprises a combination of features and advantages that overcome various problems, deficiencies, or shortcomings associated with prior devices. The various features and advantages of the invention will be readily apparent to those skilled in the art upon referring to the accompanying drawings and reading the following detailed description of the preferred embodiments of the invention.

BRIEF DESCRIPTION OF THE DRAWINGS

For a more detailed description of preferred embodiments of the present invention, reference will now be made to the accompanying drawings, wherein.

DETAILED DESCRIPTION OF PREFERRED EMBODIMENTS

Figure 1:
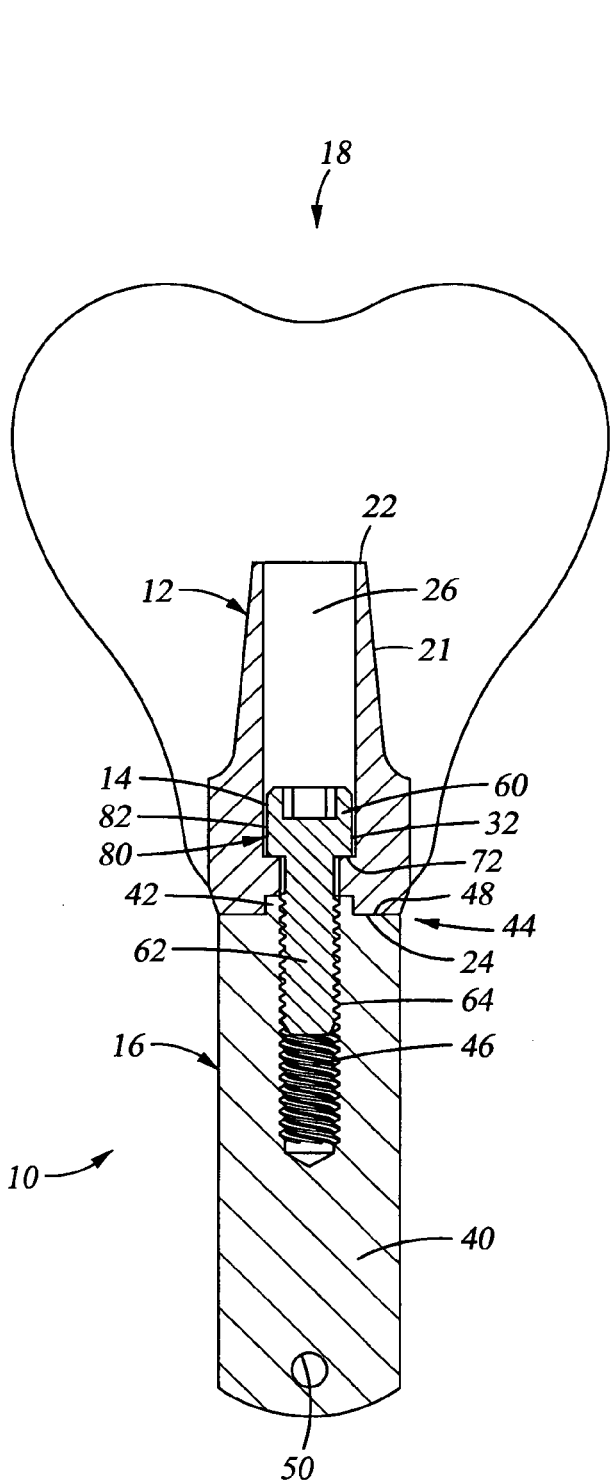
FIG. 1 is a partial cross-sectional view of a dental implant system supporting a prosthetic tooth and having a retaining screw in accordance with a preferred embodiment of the invention.

FIG. 1 illustrates a dental prosthetic implant system 10 having features in accordance with one preferred embodiment of the present invention. The dental implant system 10 generally comprises a dental component 12 (shown as an abutment), a retaining screw or bolt 14 (shown as an abutment retaining screw), and a dental implant, fixture, or root 16. The dental implant 16 is adapted to be received in a hole, osteotomy, or alveolar cavity in a jawbone of a patient. The retaining screw 14 serves the purpose of fastening the abutment 12 to the implant 16.

The dental component 12 and retaining screw 14 can be commercialized as a dental kit. This dental kit may further include additional dental components known to those skilled in the art. Such dental components include dental copings, analogs, healing collars, healing abutments, cuffs, prosthesis, and the like.

In one preferred embodiment, the dental implant system 10 further comprises a dental restoration, prosthesis, or artificial tooth 18 The abutment 12 supports the restoration 18 in the mouth of a patient. The restoration 18 can be cemented to the abutment 12. Alternatively, or in addition, a separate screw (not shown) can be used to mount and retain the prosthesis 18 on the abutment 12.

Figure 4:
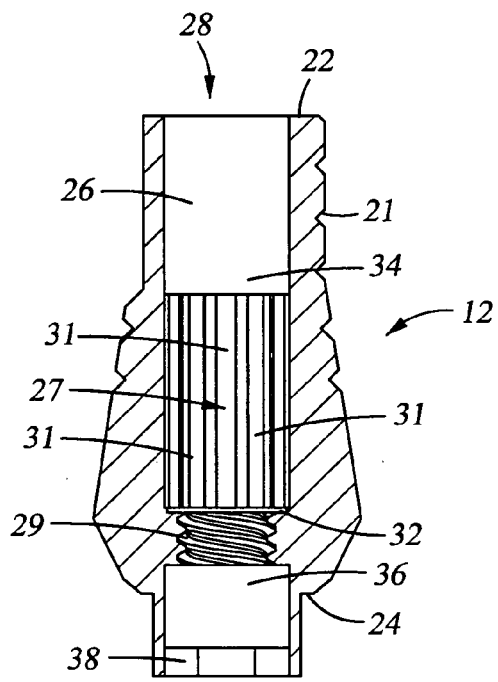
FIG. 4 is a cross-sectional view of one embodiment of an abutment according to the invention.

As shown in FIGS. 1 and 4, the abutment 12 is generally elongated in shape and can have a variety of shaped exterior surfaces 21 adapted to seat and retain the prosthesis 18. For example, the abutment exterior surface 21 can be tapered, conical, cylindrical, straight, angled, contoured, or combinations thereof.

As the skilled artisan will recognize, the present invention can be embodied utilizing a wide variety of commercially available abutments. Thus, the abutment 12 can comprise, for example, the UCLA abutment or abutments sold by Centerpulse Dental Inc. of Carslbad, Calif.

The abutment 12 has a top end 22, a bottom seating end/surface 24 for interfacing or abutting with the implant 18, and an internal, through cavity or bore 26. This cavity has a generally circular opening 28 at the top end 22 and is adapted to receive the retaining screw 14. The cavity 26 further includes an internal seating surface, shoulder, seat, or ledge 32 that serves as a seating surface for the head of the screw 14. Preferably, the shoulder 32 is generally flat, annular or ring-like in shape, but other embodiments are known to those skilled in the art.

The shoulder or abutting surface 32 divides or partitions the through cavity 26 into an upper generally cylindrical cavity, portion, or surface 34 and a lower (or middle) generally cylindrical cavity, portion, or surface 36. The cavity 34 and cavity 36 are in communication with one another with the cavity 34 having a diameter larger than that of the cavity 36.

The cavity 36 is further in communication with a generally hexagonal socket, portion, or surface 38 at the bottom end 24 of the abutment 12. The hexagonal socket 38 permits anit-rotational mating, coupling, or attachment between the abutment 12 and implant 16.

As shown in FIG. 4, cavity 26 includes a locking mechanism 27 formed along the interior surface of the bore. Preferably, the locking mechanism is formed above a threaded section 29. This locking mechanism includes a plurality of locking members 31. In this embodiment, these locking members are formed as elongated channels or grooves that extend in a longitudinal or axial direction in the interior surface of the cavity 26. Preferably, the locking members are spaced about 6° to 18° apart.

Turning back to FIG. 1, the implant 16 can any be one of a wide variety of dental implants, for example, a threaded implant, a cylindrical implant, or a tapered implant, as are known in the art, such as a tapered or straight Screw-Vent implant of Centerpulse Dental Inc. The implant 16 comprises a body or root portion 40 adapted to engage an osteotomy or alveolar cavity in the jawbone of a patient. The implant includes a hexagonal post or protrusion 42 at a top end 44. A blind internal threaded socket or bore 46 originates from the top end 44 and into the implant body portion 40. The threaded socket 46 is adapted to threadably engage the abutment retaining screw 14. A seating surface 48 generally circumscribes the hexagonal post 42 to engage, contact, or abut against the opposing abutment seating surface 24. The implant body portion 40 may include a passage 50 formed to permit in-growth of bone and tissue for locking or anchoring the implant 16 in the osteotomy.

The hexagonal post 42 of the implant is configured to provide anti-rotational engagement with the abutment hexagonal socket 38 (FIG. 4). Alternatively, a mating post may be provided at the bottom end of the abutment 12 to interlock with a corresponding mating socket at the top end of the implant 16.

Figure 2:
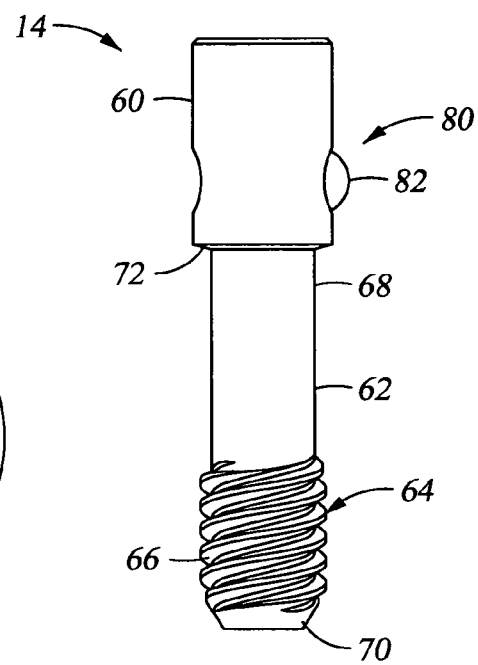
FIG. 2 is a side view of an assembled retaining screw according to the invention.
Figure 3:
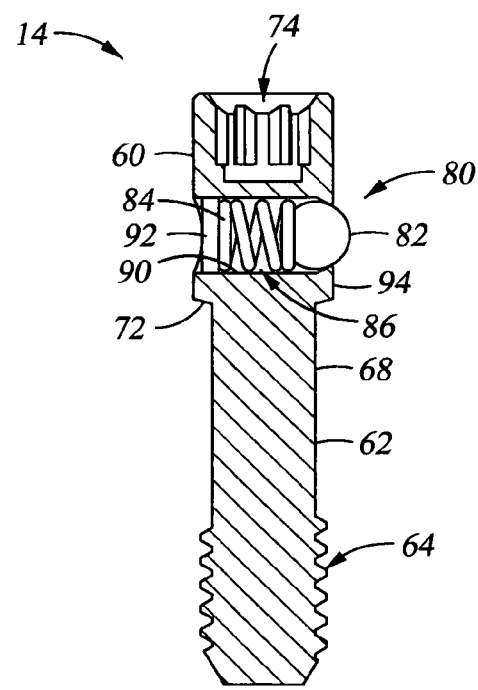
FIG. 3 is a partial cross-sectional view of a retaining screw according to the invention.

Turning now to FIGS. 1–3, the abutment retaining screw 14 is generally dimensioned and configured to adapt to a particular implant-abutment pair. The retaining screw 14 generally comprises an upper head or cap portion 60 in mechanical communication with a shank portion 62 that extends downwardly therefrom. The shank 62 comprises a threaded portion 64 having threads 66 adapted to threadably engage the threaded socket 46 of the implant 16. The threaded portion 64 is in mechanical communication with an upper non-threaded portion 68 and a lower non-threaded portion 70 of the shank 62.

The screw head 60 is preferably generally cylindrical in shape and includes a lower contacting, seating, or abutting surface 72 for engaging the opposed seating surface, or shoulder 32 of the abutment 14. Preferably, the contacting surface 72 is generally annular or ring-like in shape to generally conform to the shape of the abutment shoulder 32. Additionally, the screw head 60 preferably has a generally hexagonal cavity or socket 74 for receiving a torque wrench or other suitable tool.

Looking now to FIGS. 2 and 3, an important advantage of the present invention is illustrated. The retaining screw 14 includes a locking mechanism 80 adapted to prevent the screw from loosening. The locking mechanism includes a locking component 82 and a biasing member 84. The locking component and biasing member are located in a housing 86 that is preferably formed in the screw head 60.

The housing 86 may have various configurations known to those skilled in the art. As shown best in FIG. 3, it may be a lateral bore 90 that extends completely through the screw head 60 and that is perpendicular to a longitudinal axis of internal cavity 26. Alternatively, the bore could merely extend partially into the screw head and not completely through it.

A stop member or plug 92 closes one end of the bore 90 and maintains the biasing member 84 and locking component 82 in the housing 86. The other end of the bore remains open. A ledge or lip 94 at the end of bore 90 prevents the locking component 82 from exiting the housing while under bias from the biasing member.

As shown in FIG. 3, the biasing member 84 is a coiled spring, and the locking component 82 is a ball or ball bearing. Preferably, the ball is formed of a hard material, such as ceramic, ruby, or silicone nitride. Preferably, the spring is formed of a biocompatible, corrosive resistant material, such as titanium. Other materials include stainless steel (such as SS 17-4) coated with an amorphous diamond coating. Preferably, the spring is biocompatible and corrosive resistant.

Figure 5:
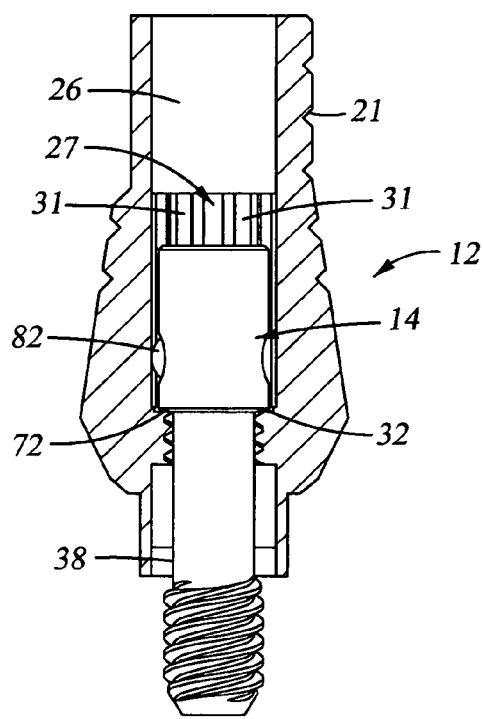
FIG. 5 is a partial cross-sectional view showing the abutment of FIG. 4 with the retaining screw of FIG. 2.

Turning now to FIGS. 3 and 5, the coupling between the retaining screw 14 and abutment 12 is shown in detail. The locking mechanism 86 of the screw engages or locks with the locking mechanism 27 of the abutment. Specifically, when the abutting surface 72 of the screw seats with the abutting surface 32 of the abutment, the biasing member 84 biases the locking component 82 against the internal surface of the cavity. The locking component slideably moves in bore 90 in a radial direction that is perpendicular to a longitudinal axis of internal cavity 26. The locking component 82, thus, engages the locking members 31. This connection or engagement prevents the screw from loosening or losing preload while the screw is tightened or torqued with the implant.

The rotational force or torque required to disengage the locking mechanism 86 of the screw from the locking mechanism 27 of the abutment should be greater than the forces tending to loosen the screw, such as vibrational and occlusal forces like chewing, grinding, talking, brushing, etc.

One skilled in the art will appreciate that the biasing member and locking component can have various configurations and continue to function as a locking mechanism on the screw. The locking component, for example, can be a pin, a button, a cylinder, other geometric configurations, or combinations thereof FIG. 6 shows one such alternate embodiment.

Figure 6:
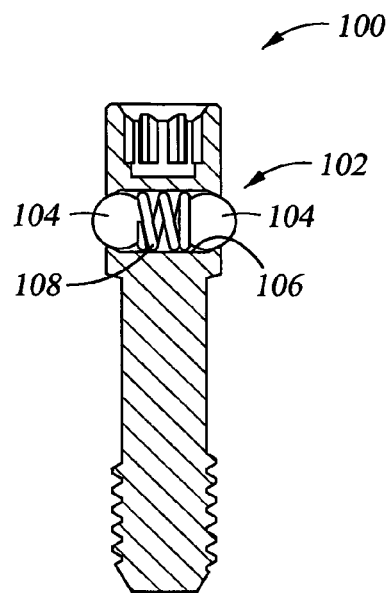
FIG. 6 is a partial cross-sectional view of another embodiment of a retaining screw according to the invention.

FIG. 6 shows a retaining screw 100 similar to the screw in FIGS. 2 and 3. One difference is with the locking mechanism 102. Here, the locking component 104 includes two separate balls. Each ball is positioned at one end of bore 106 and is biased by one end of biasing member 108. A ledge, lip, or stop member 112 at each end of the bore prevents the locking components from escaping the bore.

It will be appreciated that the present invention could incorporate multiple locking components and biasing members in other configurations as well. Multiple bores, for example, could be used to house multiple locking components and biasing members.

Figure 7:
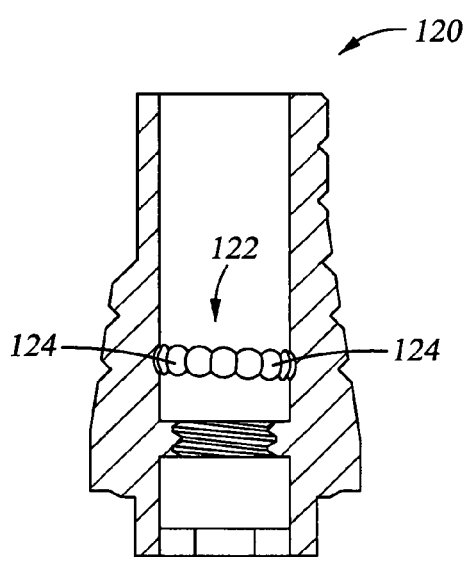
FIG. 7 is a cross-sectional view of another embodiment of an abutment according to the invention.

Although FIG. 4 shows the locking members 31 as channels, one skilled in the art will appreciate that the locking mechanism 27 can have various configurations without departing from the scope of the invention. FIG. 7, for example, shows an abutment 120 similar to the abutment 12 in FIG. 4. This abutment 120, however, has a different locking mechanism 122. Here, the locking mechanism 122 includes a plurality of locking members 124 formed as circular indentations or partial spherical indentations. These indentations could have various configurations, such as squares, spheres, rectangles, or other polygonal formations.

The present invention can be used with various dental implants and dental accessories, such as abutments, healing components, fixture mounts, copings, analogs, cuffs, or other dental components. Further, as understood by those skilled in the art, the precise configuration and dimensions of the various components of the retaining screw may vary depending upon the size of the implant or dental component. The principles of the present invention can be applied to these various components. Further yet, while preferred embodiments of this invention have been shown and described, modifications thereof can be made by one skilled in the art without departing from the spirit or teaching of this invention.

What is claimed is:

1. A dental kit attachable to a coronal end of a dental implant, the kit comprising:
    a dental component having an internal cavity with a seating surface and a locking mechanism; and
    a dental retaining screw having a head adapted to engage the seating surface of the dental component and tighten the dental component to the dental implant, the head including a moveable locking component and a biasing member, wherein the biasing member biases the locking component against the locking mechanism to prevent the retaining screw from loosening while the retaining screw is threadably engaged with the dental implant.

2. The dental kit of claim 1 wherein the locking mechanism is located on the internal cavity and is one of a partial sphere, square, groove, channel, or indentation.

3. The dental kit of claim 2 wherein the locking component is a ball bearing, and the biasing member is a spring.

4. The dental kit of claim 3 wherein the ball is formed of ceramic, and the spring is formed of titanium.

5. The dental kit of claim 1 wherein the dental retaining screw includes a bore housing the locking component and biasing member.

6. The dental kit of claim 5 wherein the internal cavity has a longitudinal axis, and the bore is perpendicular to the axis.

7. The dental kit of claim 6 wherein the biasing member biases the locking mechanism partially out of the bore and into the internal cavity to engage the locking mechanism.

8. The dental kit of claim 7 wherein the biasing member is a coiled spring, and the locking mechanism is a ball bearing.

* * * * *